(12) United States Patent
Nickeson et al.

(10) Patent No.: US 11,672,922 B2
(45) Date of Patent: Jun. 13, 2023

(54) DISTAL NEEDLE AND STYLET TIPS

(71) Applicant: Gyrus ACMI Inc., Southborough, MA (US)

(72) Inventors: Matthew E. Nickeson, Seattle, WA (US); Christopher R. Ralph, Woodinville, WA (US)

(73) Assignee: Gyrus ACMI, Inc., Westborough, MA (US)

( * ) Notice: Subject to any disclaimer, the term of this patent is extended or adjusted under 35 U.S.C. 154(b) by 0 days.

(21) Appl. No.: 17/028,247

(22) Filed: Sep. 22, 2020

(65) Prior Publication Data

US 2021/0093800 A1 Apr. 1, 2021

Related U.S. Application Data

(60) Provisional application No. 62/906,470, filed on Sep. 26, 2019.

(51) Int. Cl.
*A61M 5/32* (2006.01)
*A61M 5/31* (2006.01)

(52) U.S. Cl.
CPC ........ *A61M 5/3291* (2013.01); *A61M 5/3202* (2013.01); *A61M 2005/311* (2013.01)

(58) Field of Classification Search
CPC .............. A61M 5/3291; A61M 5/3202; A61M 2005/311; A61M 2025/0063; A61M 25/0102; A61M 2025/0024; A61M 2025/105; A61M 2025/1095
See application file for complete search history.

(56) References Cited

U.S. PATENT DOCUMENTS 5,458,614 A * 10/1995 Humphrey .............. A61M 5/32
604/239
2001/0023333 A1* 9/2001 Wise ...................... A61M 25/10
604/99.01

FOREIGN PATENT DOCUMENTS

WO WO-2005046773 A1 * 5/2005 .......... A61M 11/007

* cited by examiner

*Primary Examiner* — Theodore J Stigell
*Assistant Examiner* — Rachel T. Smith
(74) *Attorney, Agent, or Firm* — Schwegman Lundberg & Woessner, P.A.

(57) ABSTRACT

Disclosed embodiments include apparatuses and methods for using a tip member to deposit or collect a supply of material from within a body. In an illustrative embodiment, an apparatus includes a tip body defining an annular chamber. A tip receptacle is configured to be joinable with a lumen and to receive a fluid flow therethrough and to convey the fluid flow into the annular chamber. A material distribution element is fluidly coupled with the annular chamber, wherein when the fluid flow is introduced into the annular chamber. The material distribution element diffusively passes the fluid flow out of multiple egress points in at least one of a distal end and a lateral surface of the tip body.

8 Claims, 10 Drawing Sheets

DISTAL NEEDLE AND STYLET TIPS

PRIORITY CLAIM

The present application claims the priority and benefit of U.S. Provisional Patent Application Ser. No. 62/906,470 filed Sep. 26, 2019 and entitled "DISTAL NEEDLE AND STYLET TIPS."

FIELD

The present disclosure relates to distal needle tips for insertion of material into a body or collection of matter from a body.

BACKGROUND

The statements in this section merely provide background information related to the present disclosure and may not constitute prior art.

Depositing material at a particular target location in a body may be problematic. It may be difficult to convey a supply of material at the desired location and to release the material in a controlled fashion—particularly where the target location is not immediately below a surface of the skin. The material may seep out of the implement that conveys the material before the implement reaches the target location. Further, even if the material is conveyed to the target location, depositing the material in a controlled manner may be difficult.

SUMMARY

Disclosed embodiments include apparatuses and methods for conveying and disbursing a supply of material into a body and collecting a supply of material within a body.

In an illustrative embodiment, an apparatus includes a tip body defining an annular chamber. A tip receptacle is configured to be joinable with a lumen and to receive a fluid flow therethrough and to convey the fluid flow into the annular chamber. A material distribution element is fluidly coupled with the annular chamber, wherein when the fluid flow is introduced into the annular chamber. The material distribution element diffusively passes the fluid flow out of multiple egress points in at least one of a distal end and a lateral surface of the tip body.

In another illustrative embodiment, a tip body defines a fluid chamber and receives a stylet therethrough. A movable member is coupleable to the stylet, wherein extension of the stylet moves the movable member to open the fluid chamber.

In a further illustrative embodiment, a tip body defines a fluid chamber and receives a rotatable auger therethrough. A movable member is coupleable to the auger, wherein rotation of the auger moves the movable member to open the fluid chamber.

In still another illustrative embodiment, a method includes positioning a distal tip defining a fluid chamber at a distal end of a lumen. The fluid chamber is movably closed with an end member coupled to a stylet received through a lumen and into the fluid chamber. A supply of material is received into the fluid chamber. The distal tip that defines the fluid chamber is inserted at a target location in the body. The stylet is extended to advance the end member to uncap the fluid chamber.

In yet another illustrative embodiment, a method includes rotatably receiving an auger within a tip member at an end of a lumen. The auger is then rotated to one of rotatably deposit a supply of material received in the tip member and rotatably collecting a supply of material from adjacent the tip member.

Further features, advantages, and areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way. The components in the figures are not necessarily to scale, with emphasis instead being placed upon illustrating the principles of the disclosed embodiments. In the drawings:

FIGS. 9A-24 are side plan views in partial cutaway of various tips for diffusely depositing a supply of material at or collecting a supply of material from the target location;

DETAILED DESCRIPTION

The following description is merely illustrative in nature and is not intended to limit the present disclosure, application, or uses. It will be noted that the first digit of three-digit reference numbers and the first two digits of four-digit reference numbers correspond to the first digit of one-digit figure numbers and the first two digits of two-digit figure numbers, respectively, in which the element first appears.

The following description explains, by way of illustration only and not of limitation, various embodiments of apparatuses and methods for depositing a supply of material at or collecting a supply of material from locations within a body. Various embodiments include distal tips fluidly coupleable to a supply of fluid, such as may be supplied via a lumen from a syringe or other source, where the distal tips are configured to diffusely disperse a flow of fluid. Other embodiments include a movable tip controlled by an elongated stylet to open a fluid chamber to deploy the material. Still other embodiments include a tip that received a rotatable auger to deposit or collect a supply of material. Other embodiments include methods of using the same.

Figure 1:
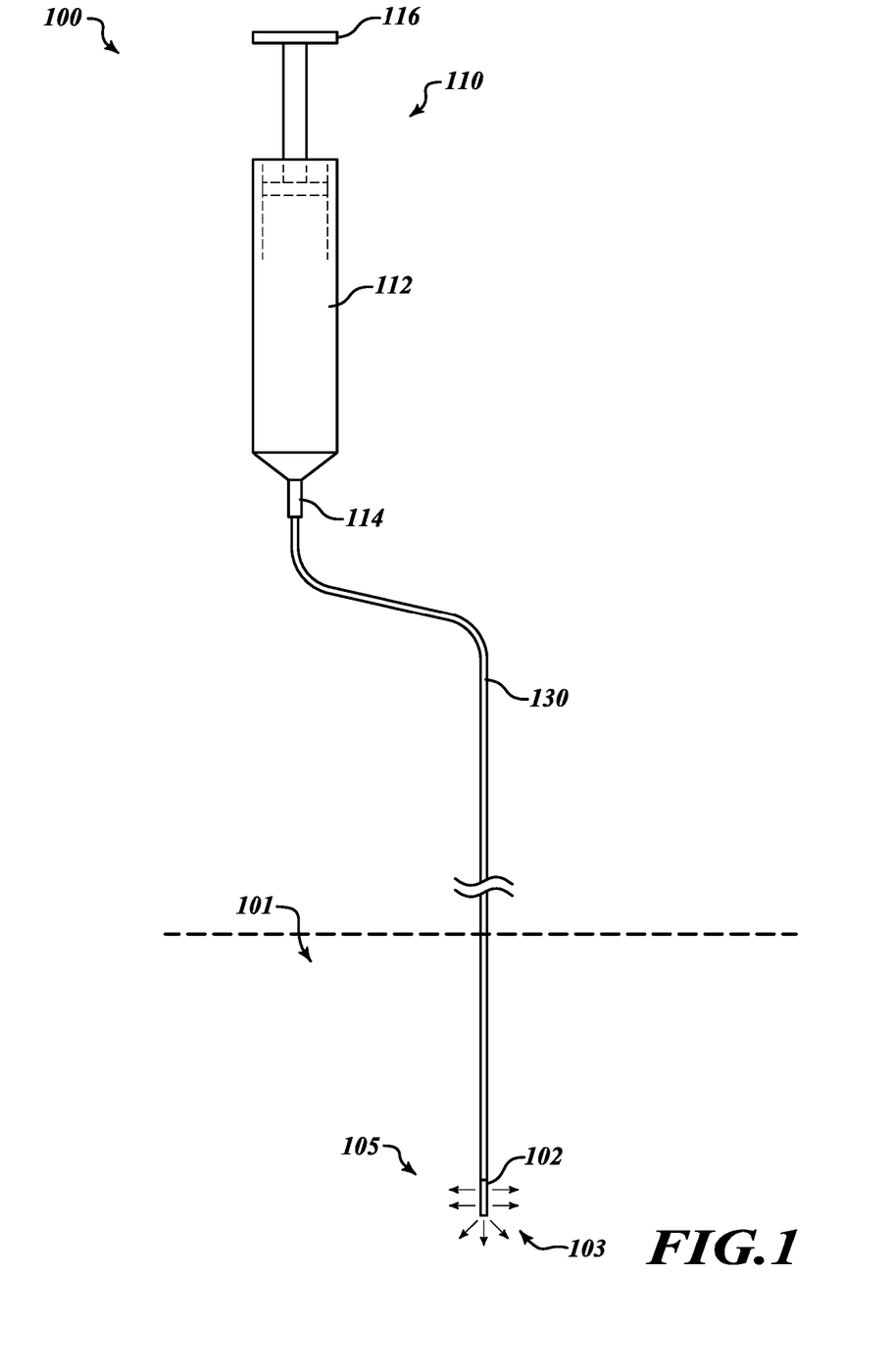
FIG. 1 is a schematic view of an illustrative system for depositing a supply of material at or collecting a supply of material from a target location within a body.

Referring to FIG. 1, a system 100 includes a distal tip 102 fluidly couplable to a fluid source 110 via a lumen 130. The distal tip 102, as further described with reference to FIGS. 2-7, is configured to disburse a flow of fluid 103 at a target location 105 within a body 101. The distal tip 102 is fluidly couplable to the fluid source 110 via the lumen 130, which may include a flexible tube, such as a plastic, rubber, or metal tube. The lumen 130 is coupled to the fluid source 110 at a port 114. Where the fluid source 110 is a syringe, for example, the fluid source includes a fluid reservoir 112 that is actuated by a plunger 116 to drive a flow of fluid (not shown in FIG. 1) from the fluid reservoir 112 to the port 114 and into the lumen 130 where it is conveyed to the distal tip 102.

Referring to FIGS. 2-7, various embodiments of distal tips provide for a diffuse disbursement of fluid at a target location within a body. For example, the distal tips may include various configurations for distributing material received into an annular chamber within the distal tip and diffusively disbursing that material.

Figure 2:
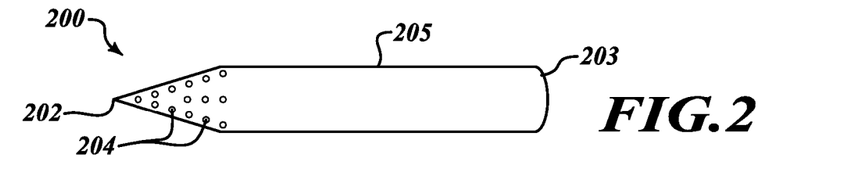
FIGS. 2-7 are side plan views of various illustrative tips for diffusely depositing a supply of material at the target location.

Referring to FIG. 2, a distal tip 200 includes an annular chamber 205 and a pointed distal end 202 opposite a fluid receptacle end 203. The distal tip 200 defines an annular chamber therein that receives a flow of fluid from the fluid receptacle end 203. The material distribution element includes a number of fluid holes 204 in the distal end 202 through which fluid supplied into the annular chamber may be diffusely disbursed. With the pointed distal end 202, the distal tip 200 is suited for applications where the distal tip 200 may need to pierce tissue to reach a target location.

It will be appreciated that each of the distal tips of FIGS. 3-7 includes a fluid receptacle end to receive a flow of fluid and supply the flow of fluid into an annular chamber defined by the tips. The following description of the distal tips of FIGS. 3-7 thus will focus on the material distribution element of each of the distal tips.

Figure 3:
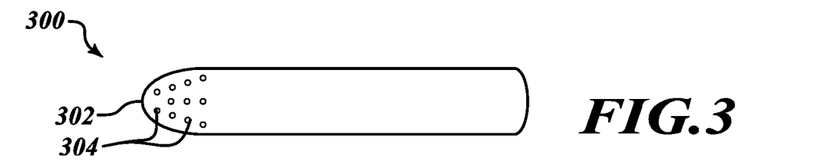

Referring to FIG. 3, a distal tip 300 includes a rounded distal end 302. The material distribution element includes a number of fluid holes 304 in the distal end 302 through which fluid supplied into the annular chamber may be diffusely disbursed. With the rounded distal end 302, the distal tip 300 is suited for applications where it is undesirable to potentially pierce or cut tissue, as may occur with the pointed distal end 202 of the distal tip of FIG. 2.

Figure 4:
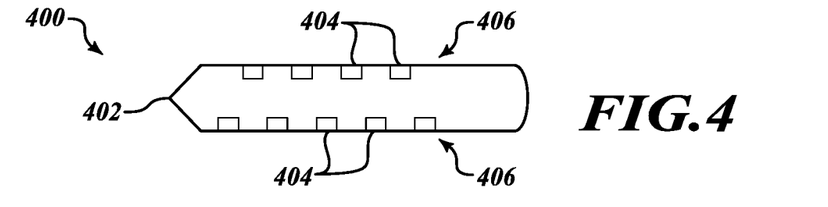
Figure 5:
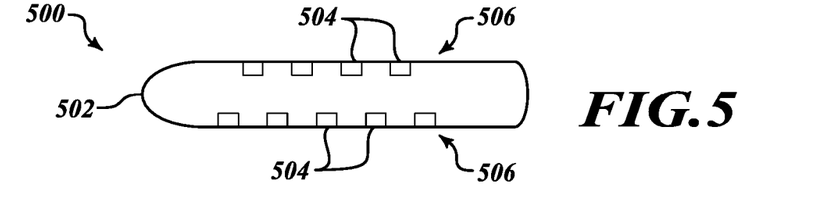

Referring to FIG. 4, a distal tip 400 includes a partially blunted distal end 402. In contrast to the end-based material distribution element of distal tips 200 and 300 of FIGS. 2 and 3, respectively, the material distribution element includes a number of laterally-disposed slots 404 along sides 406 of the distal tip 400. In contrast to the distal tips 200 and 300, which distribute fluid from the ends 202 and 302, respectively, the distal tip 400 distributes fluid from the sides 406. The partially blunted end 402 may be useful where some penetration of the distal tip 400 is desirable.

Figure 6:
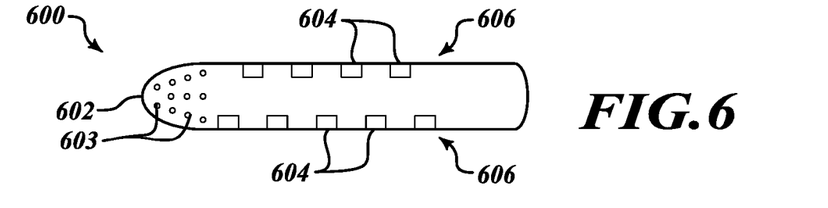

It will be appreciated that features of the disclosed embodiments may be combined to achieve desirable results for various applications. For example, and referring to FIG. 5, a distal tip 500 includes a rounded distal end 502 (like that of the distal tip 300 of FIG. 3). However, the distal tip 500 includes laterally-disposed slots 504 along sides 506 (like the distal tip 400 of FIG. 4). Referring to FIG. 6, a distal tip 600 includes a rounded distal end 602 (like that of the distal tips 300 and 500 of FIGS. 5 and 6, respectively). The distal tip 600 also includes end-based fluid holes 603 (like the distal tips 200 and 300 of FIGS. 2 and 3, respectively) as well as laterally-disposed slots 604 along the sides 606 of the distal tip 600 (like the distal tips 400 and 500 of FIGS. 400 and 500). Desirable features of different embodiments may be combined to reach a desirable configuration without limitation.

Figure 7:
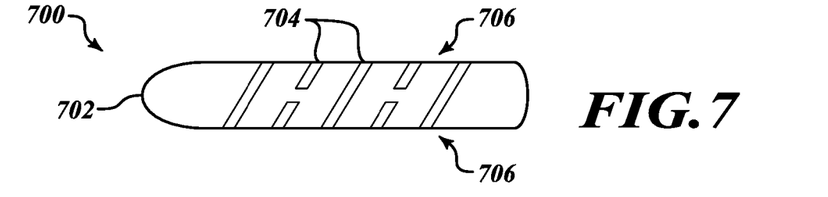

In addition, other types of material distribution elements may be used. Referring to FIG. 7, diagonally cut slots 704 (which may be molded or mechanically cut or drilled, as in other material distribution elements) are arrayed along lateral sides 706 of the distal tip 700. The slots 704, which may be larger than the holes 204 (FIG. 2) or the slots 504 and 604 (FIGS. 5 and 6) may provide for a large volume of fluid distribution or a very diffuse distribution to suit a particular application where these aspects are desirable. The distal tip 700 also includes a rounded distal end 702 (like distal tip 500).

Figure 8:
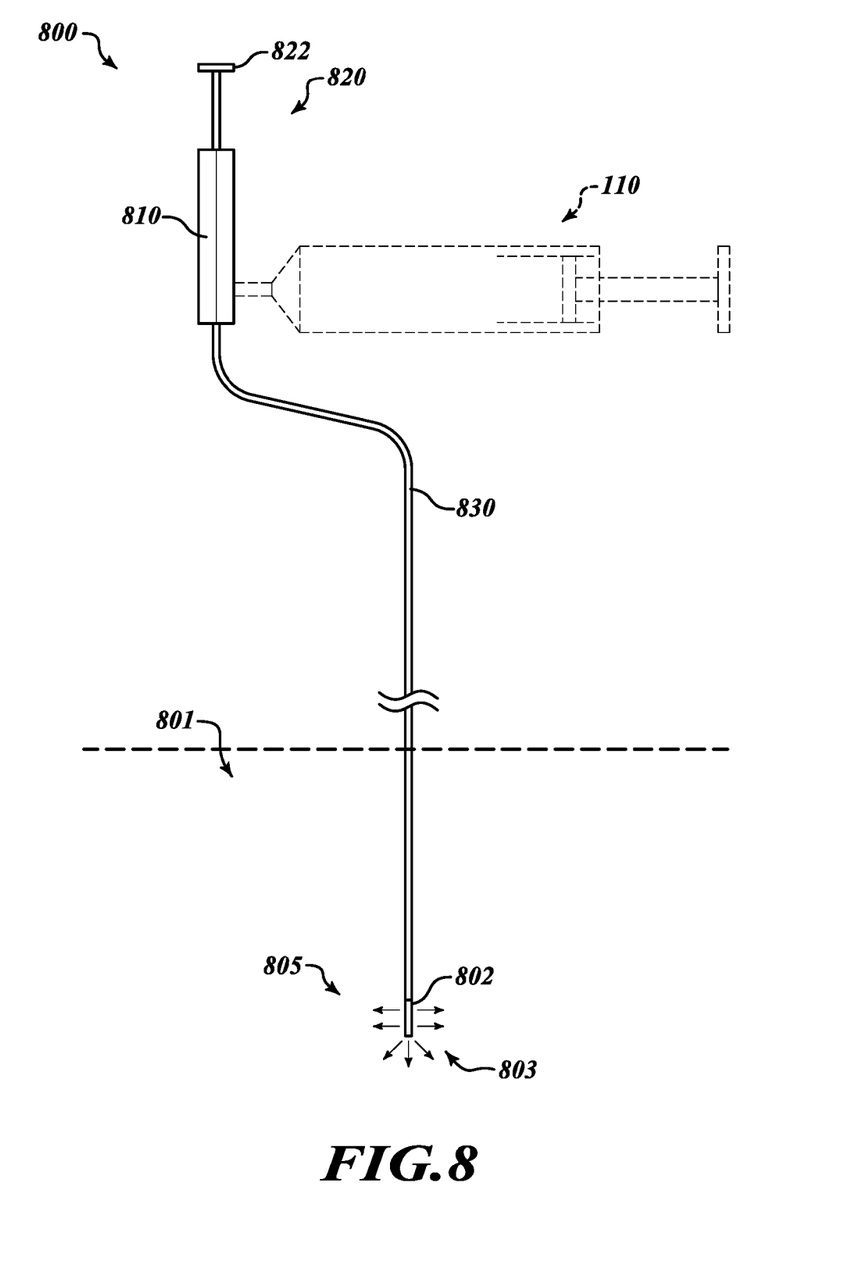
FIG. 8 is a schematic view of another illustrative system for depositing a supply of material at or collecting a supply of material from a target location within a body.

Referring to FIG. 8, a system 800 includes a distal tip 802 that is optionally couplable to a fluid source 110 via a lumen 830. The distal tip 802, as further described with reference to FIGS. 9A-24, is configured to provide a diffuse flow of fluid 803 at a target location 805 within a body 801. The distal tip 802 may be fluidly couplable to the fluid source 110 via the lumen 830, or the distal tip 802 may be charged with a supply of fluid or other material prior to the distal tip 803 being inserted into the body 801. According to various embodiments further described below, the distal tip is opened or otherwise manipulated to disgorge its contents with a stylet mechanism 820 that extends a stylet (not shown in FIG. 8) through the lumen 830 to the distal tip 802. A plunger 822 or other mechanism may be used to actuate the stylet to extend the stylet to cause the distal tip 802 to disburse its contents. In applications where it is desirable to supply the distal tip with fluid from the fluid source 110, the fluid source 110 and the stylet mechanism 820 may be coupled at a junction 810 that is coupled to an interior of the lumen 830. As a result, both a supply of fluid from the fluid source and the stylet may coextend to the distal tip 802 through the lumen 830.

Figure 9A:
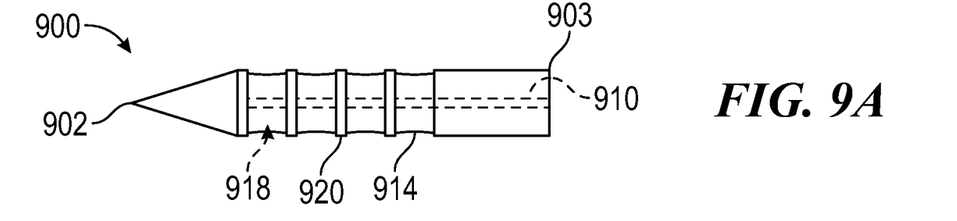
Figure 9B:
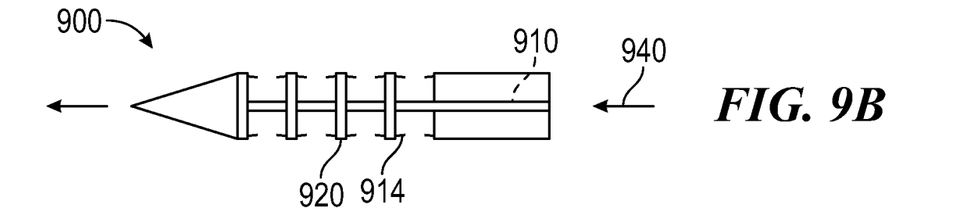

Referring to FIGS. 9A-24, any number of configurations of distal tips may be activated or controlled by a stylet to deploy a fluid or other supply of material. Referring to FIGS. 9A and 9B, a distal tip 900 includes a pointed distal end 902 that is coupleable with a stylet 910 and is at an end of the distal tip 900 opposite of a base 903 that is configured to receive the stylet 910. It will be appreciated that each of the embodiments of distal tips described with reference to FIGS. 9A-24 includes a base end configured to slidably receive a stylet therethrough.

Between the pointed distal end 902 and the base 903, a number of baffles 920 are arrayed along the stylet 910. A destructible membrane 914, such as a layer of heat shrink, is affixed from the distal end 902 across the baffles 920 to the base 903, thereby forming a fluid chamber 918. In some embodiments the fluid chamber 918 could be filled from the base 903 in fluid communication with the lumen or another fluid supply (not shown in FIG. 9A). In some other embodiments, the fluid chamber 918 could be filled before the destructible membrane 914 is installed to seal the fluid chamber 918.

Referring to FIG. 9B, a force 940 is applied to the stylet 910 to cause the stylet 910 to be extended. Extension of the stylet 910 moves the distal tip 902, thereby straining and rupturing the destructible membrane 914. The rupturing of the destructible membrane 914 thus allows the contents of the fluid chamber (FIG. 9A) to seep out of the fluid chamber. The contents of the fluid chamber 918 are thus released all around the distal tip 900 and are not driven out of one or more hypodermic ports under pressure.

Figure 10A:
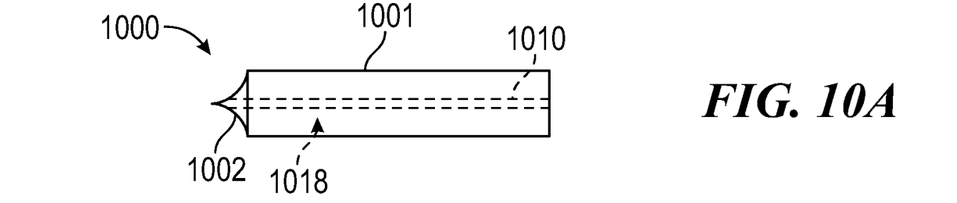
Figure 10B:
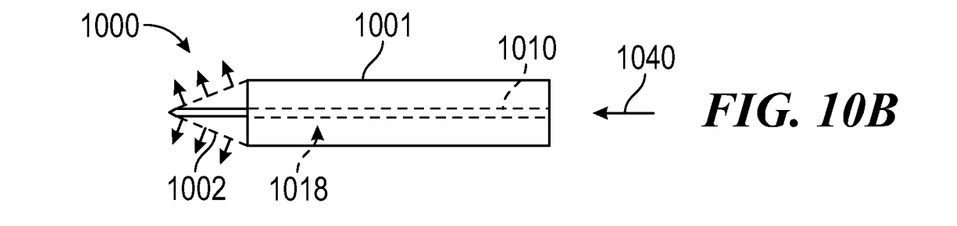

Referring to FIG. 10A, another embodiment of a distal tip 1000 includes a tip member 1001 that defines a fluid chamber 1018 and through which a stylet 1010 extends to a cap 1002. The cap 1002 is formed of a semi-permeable membrane that sealably closes the fluid chamber 1018 within the tip member 1001 until the distal tip 1002 is distended. Referring to FIG. 10B, the stylet 1010 is extended upon application of a force 1040 to the stylet 1010. As the stylet 1010 is extended against the semi-permeable membrane at the tip 1002, the semi-permeable membrane becomes distended and ruptures or becomes permeable, thereby permitting the release of fluid contained in the fluid chamber 1018.

Figure 11A:
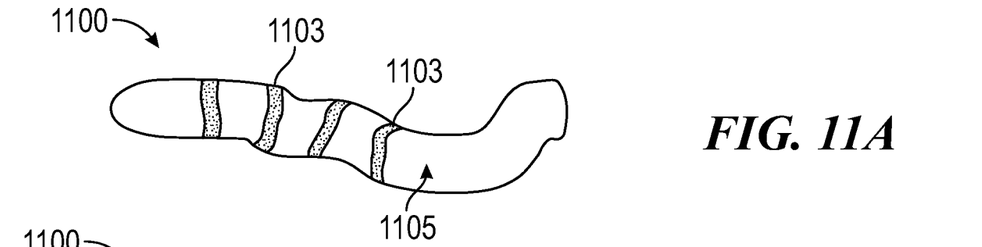
Figure 11B:
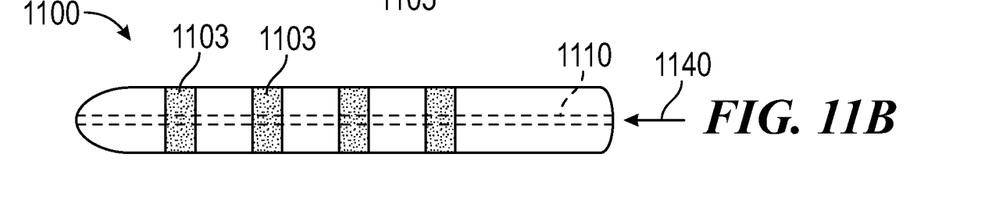

Referring to FIG. 11A, a collapsible tip 1100 includes a flexible, annular member that includes semi-permeable membranes 1103 along a length 1105 of the collapsible tip 1100. Like the cap 1002 of the distal tip 1000, semi-permeable membranes may become porous or rupture upon being distended. Referring to FIG. 11B, the collapsible tip 1100 can be made rigid by insertion of a stylet 1110 therein. The collapsible tip 1100 also can receive a supply of fluid therein. Upon application of a force 1140 to extend the stylet 1110, the semi-permeable membranes 1103 become distended and release the fluid contents of the distal tip 1103 into the surrounding area.

Referring to FIGS. 12A-24, various embodiments of distal tips include a movable member at an end of the distal tip that may be used to cap an end of the tip body to seal a fluid chamber defined therein. Extending a stylet extends the movable member to open the fluid chamber, and retracting the stylet retracts the movable member to close the fluid chamber. The movable members have different shapes both facing outward away from the tip body and facing toward the tip body to seal the fluid chamber and to redirect fluid flow from the fluid chamber to diffusely disperse the contents thereof. The embodiments of FIGS. 12A-24 may be used with a fluid source 110, as described with reference to FIG. 8, to diffusely disburse a fluid flow from the fluid source 110 or to disburse material captured within the fluid chamber defined by the tip body.

Figure 12A:
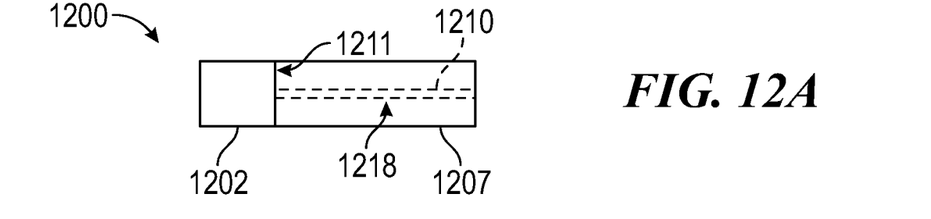
Figure 12B:
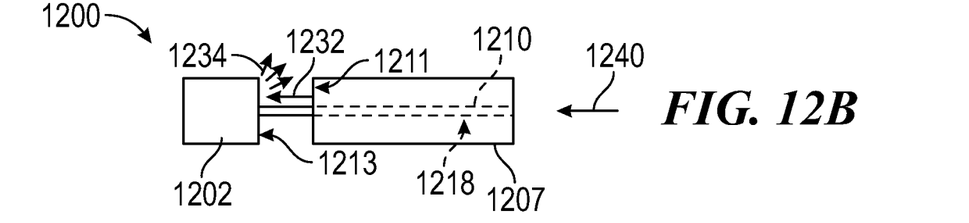

Referring to FIG. 12A, distal tip 1200 includes a movable member 1202 is coupleable with a stylet 1210 and is disposed to sealably close an end 1211 of a tip body 1207 that defines a fluid chamber 1213. Referring to FIG. 12B, a force 1240 is applied to the stylet 1210 to cause the stylet 1210 to be extended. Extension of the stylet 1210 moves the movable member 1202, thereby uncapping the end 1211 of the tip body 1207. The contents of the fluid chamber 1213 are thus released through the end 1211 of the tip body 1207.

A shape of the movable member 1202 may be useful in diffusing the flow of fluid—particularly when a significant flow of fluid is provided from the fluid source 110 (FIG. 8). Referring to FIG. 12B, a fluid flow 1232 expelled from the end 1211 of the tip body 1207 impacts a rearward surface 1213 of the movable member 1202 instead of jetting straight out of the tip body 1207. As a result, the fluid flow 1232 is scattered into a diffuse flow 1234.

Figure 13A:
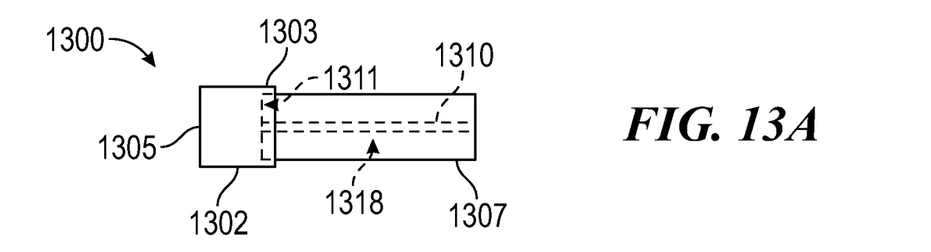
Figure 13B:
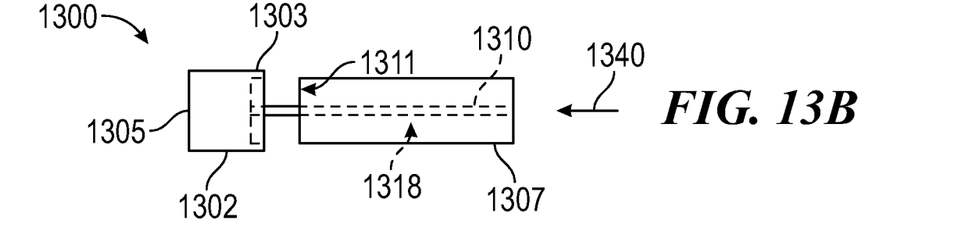

Referring to FIG. 13A, a movable member 1302 is coupleable with a stylet 1310 and is disposed to sealably close an end 1311 of a tip body 1307 that defines a fluid chamber 1318. The movable member 1302 includes an annular seal 1310 that seals against the end 1311 of the tip body 1307 and around an edge of the tip body 1307. Referring to FIG. 13B, a force 1340 is applied to the stylet 1310 to cause the stylet 1310 to be extended. Extension of the stylet 1310 moves the movable member 1302, thereby uncapping the end 1311 of the tip body 1307. The contents of the fluid chamber 1318 are thus released through the end 1311 of the tip body 1307.

Figure 14A:
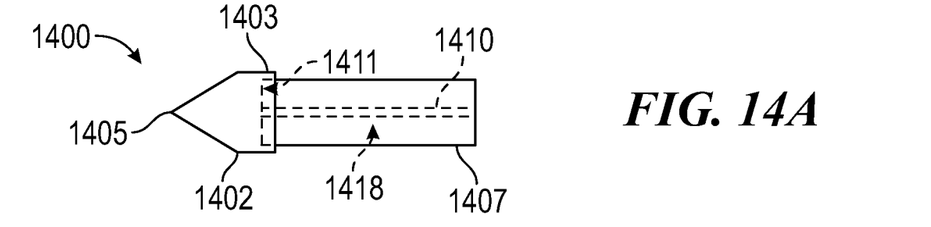

Referring to FIG. 14A, distal tip 1400 includes a movable member 1402 is coupleable with a stylet 1410 and is disposed to sealably close an end 1411 of a tip body 1407 that defines a fluid chamber 1418. Like the movable member 1302 of the distal tip 1300 of FIG. 13, the movable member 1402 includes an annular seal 1410 that seals against the end 1411 of the tip body 1407 and around an edge of the tip body 1407. Unlike the movable member 1302 (which has a blunt end 1305), however, the movable member 1402 includes a pointed end 1405. As previously described with reference to FIGS. 2-4, a pointed end 1405 may be desirable for some applications where tissue is to be pierced, while a blunted end 1305 may be desirable for applications where piercing is desirably avoided.

Figure 14B:
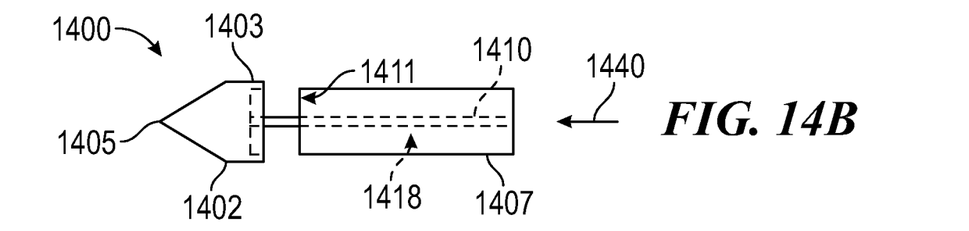

Referring to FIG. 14B, a force 1440 is applied to the stylet 1410 to cause the stylet 1410 to be extended. Extension of the stylet 1410 moves the movable member 1402, thereby uncapping the end 1411 of the tip body 1407. The contents of the fluid chamber 1418 are thus released through the end 1411 of the tip body 1407.

Figure 15A:
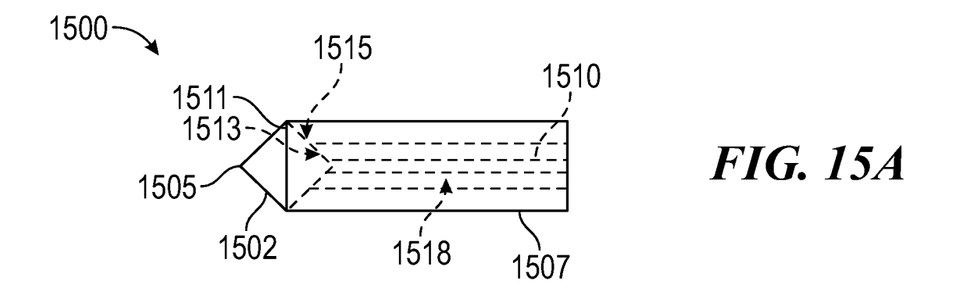

Referring to FIG. 15A, a movable member 1502 is coupleable with a stylet 1510 and is disposed to sealably close an end 1511 of a tip body 1507 that defines a fluid chamber 1518. However, instead of sealably closing against edges of a flat end 1511 of the tip body 1507, a rearward surface 1513 of the movable member 1502 is matably shaped to engage an inner surface 1515 of the tip body 1507 to seal the fluid chamber 1518. Specifically, the movable member 1502 has a conical rearward surface 1513 to engage a conical inner surface 1515 of the tip body 1507. The movable member 1502 also has a conical end 1505 which may be useful to pierce tissue or other uses where a pointed tip is desirable.

Figure 15B:
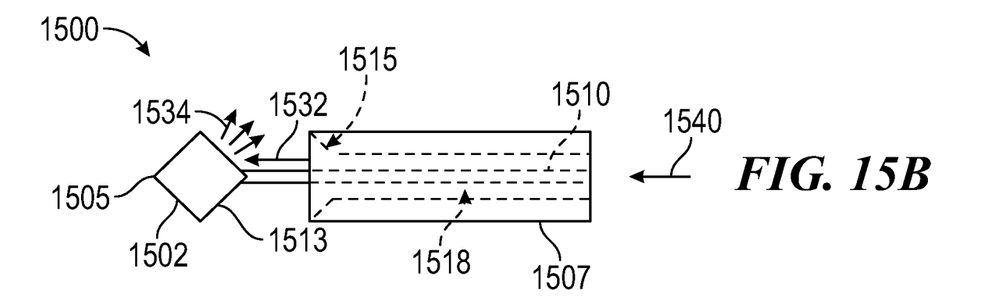

Referring to FIG. 15B, a force 1540 is applied to the stylet 1510 to cause the stylet 1510 to be extended. Extension of the stylet 1510 moves the movable member 1502, thereby uncapping the end 1511 of the tip body 1507. The contents of the fluid chamber 1518 are thus released through the end 1511 of the tip body 1507. As previously described with reference to FIG. 12, the shape of the rearward surface 1513 may be useful in diffusing the flow of fluid. The fluid flow 1532 expelled from the tip body 1507 impacts a rearward surface 1513 of the movable member 1502. As a result, the fluid flow 1532 is scattered into a diffuse flow 1534.

Figure 16A:
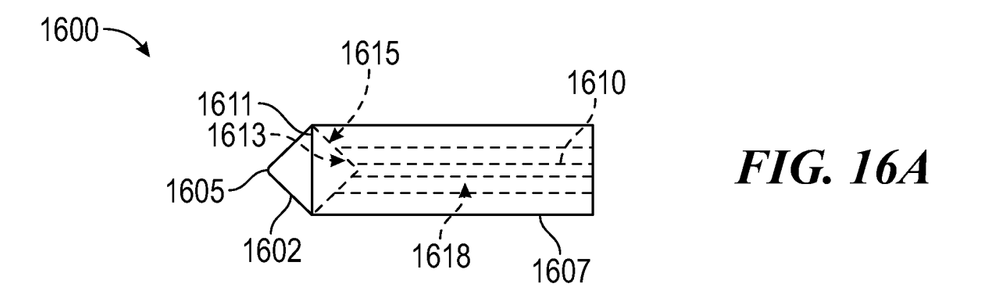

Referring to FIG. 16A, a movable member 1602 is coupleable with a stylet 1610 and is disposed to sealably close an end 1611 of a tip body 1607 that defines a fluid chamber 1618. Like the distal tip 1500 of FIG. 15, instead of sealably closing against edges of a flat end 1611 of the tip body 1607, a rearward surface 1613 of the movable member 1602 is matably shaped to engage an inner surface 1615 of the tip body 1607 to seal the fluid chamber 1618. Specifically, the movable member 1602 has a conical rearward surface 1613 to engage a conical inner surface 1615 of the tip body 1607. However, unlike the distal tip 1500 of FIG. 15, the movable member 1602 has a blunt, slightly rounded tip 1605 which may be useful when it is not desirable to potentially pierce tissue with the tip 1605.

Figure 16B:
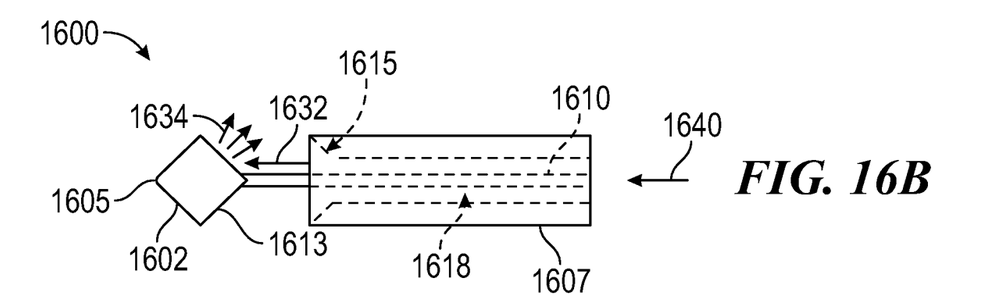

Referring to FIG. 16B, a force 1640 is applied to the stylet 1610 to cause the stylet 1610 to be extended. Extension of the stylet 1610 moves the movable member 1602, thereby uncapping the end 1611 of the tip body 1607. The contents of the fluid chamber 1618 are thus released through the end 1611 of the tip body 1607. As previously described with reference to FIGS. 12 and 15, the shape of the rearward surface 1613 may be useful in diffusing the flow of fluid. The fluid flow 1632 expelled from the tip body 1607 impacts a rearward surface 1613 of the movable member 1602. As a result, the fluid flow 1632 is scattered into a diffuse flow 1634.

Figure 17:
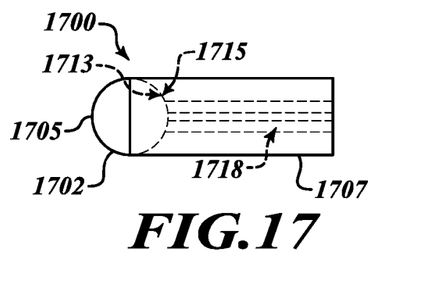
Figure 24:
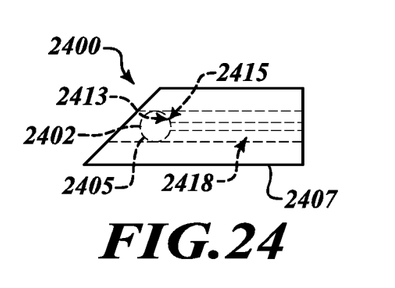

Referring to FIGS. 17-24, various other forms of movable members may be used to seal an end of tip body of a distal tip to close a fluid chamber defined therein and, when desired, to deflect a flow of fluid existing the distal tip. It will be appreciated that the configuration and operation of the embodiments of FIGS. 17 and 24 are similar to that of previously described embodiments.

Referring to FIG. 17, a movable member 1702 in a distal tip 1700 may be generally spherical in shape. Thus, the movable member 1702 has a rearward surface 1713 that matably engages a spherical inner surface 1715 of the tip body 1707 to seal the fluid chamber 1718. The spherical front surface 1705 is well-suited to applications where a smooth leading edge is desired. The rearward surface 1713 of the movable member 1702 may be used to diffusely redirect a fluid flow passing out of the distal tip 1700, as previously described with reference to FIGS. 15B and 16B.

Figure 18:
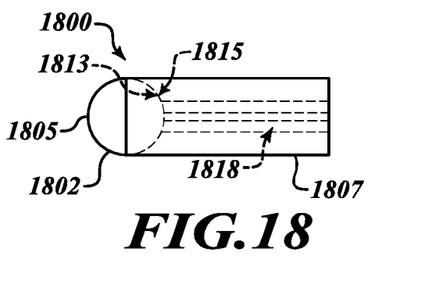

Referring to FIG. 18, a movable member 1802 in a distal tip 1800 may have a shape of a flattened spheroid. Thus, the movable member 1802 has a rearward surface 1813 that matably engages a flattened spheroidal inner surface 1815 of the tip body 1807 to seal the fluid chamber 1818. The rounded front surface 1805 is well-suited to applications where a smooth leading edge is desired. The rearward surface 1813 of the movable member 1802 may be used to diffusely redirect a fluid flow passing out of the distal tip 1800, as previously described.

Figure 19:
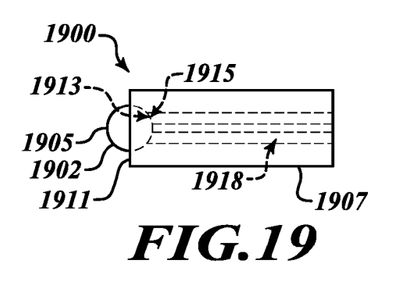

Referring to FIG. 19, a movable member 1902 in a distal tip 1900 may be in the shape of a sphere and may be sized to sealably engage an inner surface 1915 of the fluid chamber 1913 in the tin body 1907—but not be as wide as an end 1911 of the distal tip 1900. The movable member 1902 has a hemispherical rearward surface 1913 that matably engages a hemispherical inner surface 1915 of the fluid chamber 1918 to seal the fluid chamber 1913. The rounded front surface 1905 is well-suited to applications where a smooth leading edge is desired. The rearward surface 1913 of the movable member 1902 still may be used to diffusely redirect a fluid flow passing out of the distal tip 1900—even if the rearward surface 1913 is not as wide as the end 1911 of the distal tip 1900.

Figure 20:
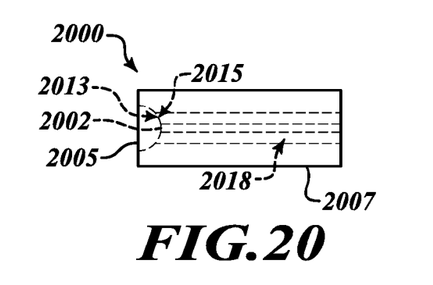

Referring to FIG. 20, a movable member 2002 in a distal tip 2000 may be in the shape of a hemisphere and may be sized to sealably engage an inner surface 2015 of the fluid chamber 2018 (but not be as wide as an end 2011 of the distal tip 200). The fluid chamber 2013 is within tip body 2007. The movable member 2002 has a hemispherical rearward surface 2013 that matably engages a hemispherical inner surface 2015 of the fluid chamber 2018 to seal the fluid chamber 2015 (as in the case of the distal tip 1900 of FIG. 19). The blunt front surface 2005 is suited to applications where a blunt leading edge is desired. Again, the rearward surface 2013 of the movable member 2002 may be used to diffusely redirect a fluid flow passing out of the distal tip 2000—even if the rearward surface 2013 is not as wide as the distal end of the distal tip 2000.

Figure 21:
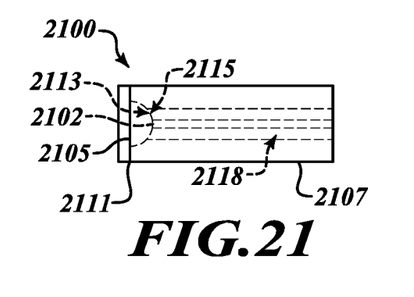

Referring to FIG. 21, a movable member 2102 in a distal tip 2100 may have a compound shape including a hemispherical rearward portion sized to sealably engage an inner surface 2115 of the fluid chamber 2113 within ti body 2107 and a panel 2105 sized to cover the end 2111 of the distal tip 2100. The movable member 2102 has a hemispherical rearward surface 2113 that matably engages a hemispherical inner surface 2115 of the fluid chamber 2218 to seal the fluid chamber 2115 (as in the distal tips 19M and 2000 of FIGS. 19 and 20). The blunt front surface presented by the panel 2105 is suited to applications where a blunt leading edge is desired. The flat panel 2105 blocks a flow of fluid from the end of the distal tip 2100 from flowing straight forward out of the distal tip 2100. Thus, the rearward surface 2113 of the movable member 2102 and the panel 2105 are useful in diffusely redirecting a fluid flow passing out of the distal tip 2100.

Figure 22:
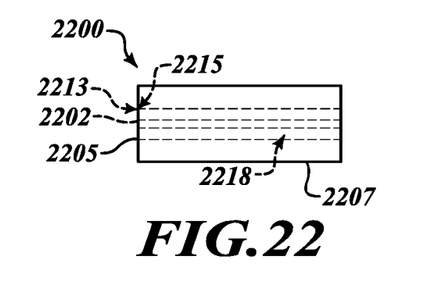

Referring to FIG. 22, a movable member 2202 in a distal tip 2200 may include only a panel 2205 sized to cover the distal end of the distal tip 2200. The blunt front surface presented by the panel 2205 is suited to applications where a blunt leading edge is desired. The flat panel 2205 is useful in partially blocking a fluid flow from passing straightforward out of the fluid chamber 2218 within the tip body 2207 of the distal tip 22000 as well as for redirecting the fluid flow. The panel 2205 can include a front surface 2213 and a back surface 2215.

Figure 23:
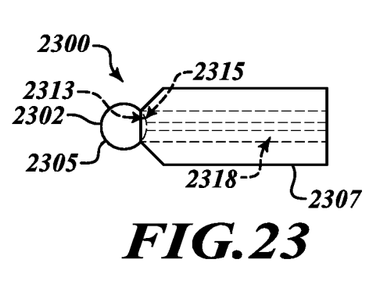

Referring to FIG. 23, it will be appreciated that a distal tip 2300 may have a forward end 2305 that does not have a flattened shape. For example, the forward end 2305 of the distal tip 2300 has a narrowed shape. Like the movable member 1902 of the distal tip 1900 of FIG. 19, the movable member 2302 has a spherical shape sized so that the rearward surface 2313 matably seals the partially hemispherical inner surface 2315 forward of the fluid chamber 2313. The rearward surface 2313 of the movable member 2302 may be useful in diffusely redirecting a flow of fluid out of the distal tip 2307.

Referring to FIG. 24, it will be appreciated that a distal tip 2400 may have an angled forward end. Also, the movable member 2402 (which is shown to be generally spherical) may be sized to fit within the angled forward end yet still block the end of the fluid chamber 2418. The rearward surface 2413 of the movable member 2402 may be useful in diffusely redirecting a flow of fluid out of the distal tip 2407. Like movable member 1900 movable member 2402 includes a partially hemispherical inner surface 2415 and a rounded front surface 2405.

Figure 25A:
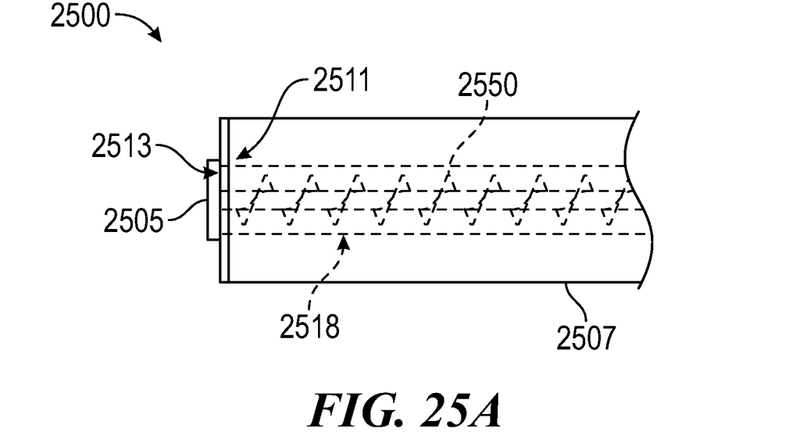
FIGS. 25A-25B are side plan views in partial cutaway of an illustrative tip receiving a rotatable auger.
Figure 25B:
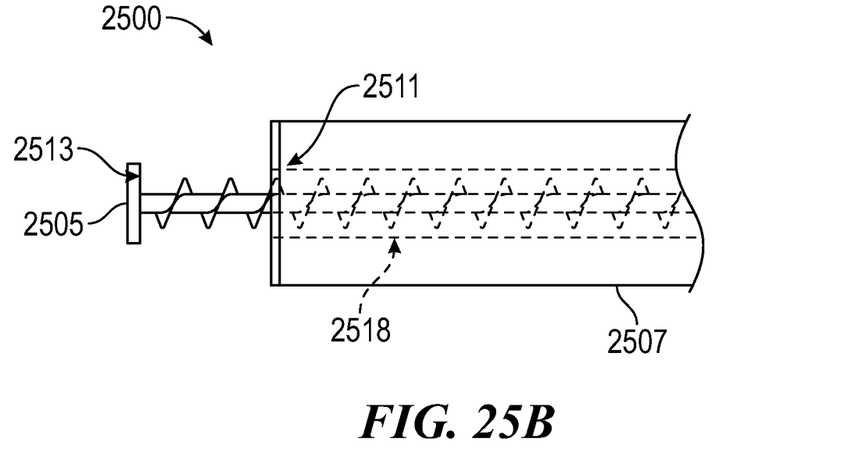

Referring to FIGS. 25A and 25B, a distal tip may receive a rotatable auger within the distal tip to move material out of or into the distal tip instead of depositing or collecting material from a distal tip with a movable member that is moved by a stylet. Referring to FIG. 25A, the distal tip 2500 as a tip body 2507 that defines a chamber 2518 through which a rotatable auger 2550 extends. If the chamber 2518 is pre-filled with material or receives material via a coupled lumen (not shown), rotation of the auger 2550 will expel the material. Conversely, if the distal tip 2500 is to be used to collect a sample, rotating the auger in the opposite direction will draw material at the forward end 2511 of the distal tip 2500 into the chamber 2518. The auger 2550 may be mated with a flat panel or other end cap 2505 configured to seal the chamber 2518 with a rearward surface 2513 before deposition of materials or after collection of materials. The flat panel 2505 may be sized and shaped to sealably engage the forward end 2511 of the distal tip 2500.

Referring to FIG. 25B, the auger 2550 may extend rearward out of the distal tip 2500 to a location where the auger 2550 can be slid to extend the auger 2550 beyond the forward end 2511 of the distal tip 2500 to deposit or collect materials. Alternatively, the auger 2550 may be joined to a rotatable stylet or cable (not shown in FIG. 25) rearward of the distal tip 2500 to rotatably and slidably motivate the auger 2550.

Figure 26:
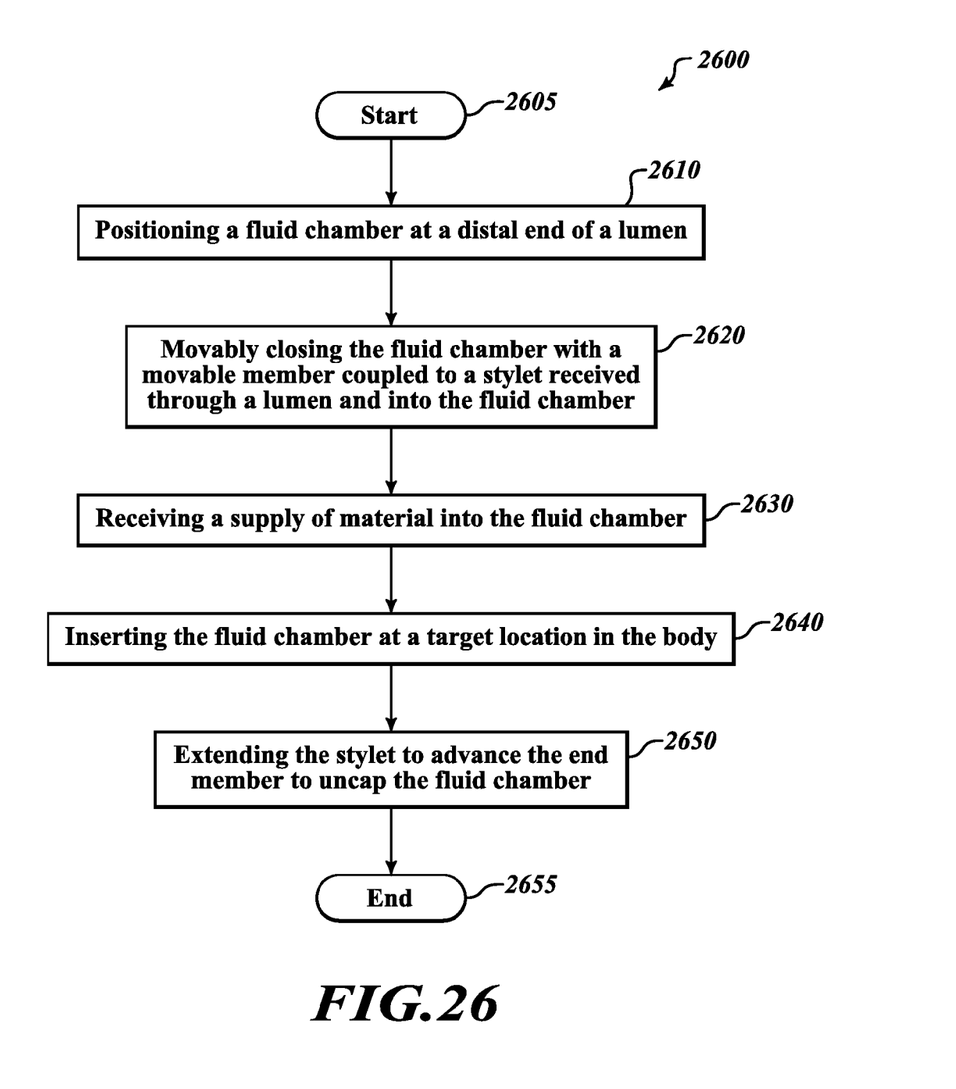
FIG. 26 is a flow diagram of an illustrative method.

Referring to FIG. 26, a flow diagram represents an illustrative method 2600 of using a distal tip with a fluid chamber sealable by a movable member coupled to a stylet to deposit materials. The method 2600 starts at a block 2605. At a block 2610, a fluid chamber is positioned at a distal end of a lumen. At a block 2620, the fluid chamber is movably closed with an end member coupled to a stylet received through a lumen and into the fluid chamber. At a block 2630, a supply of material is received into the fluid chamber. At a block 2640, the distal tip that defines the fluid chamber is inserted in the body at a target location. At a block 2650, the stylet is advanced to move the movable member to uncap the fluid chamber. The method 2600 ends at a block 2655.

Figure 27:
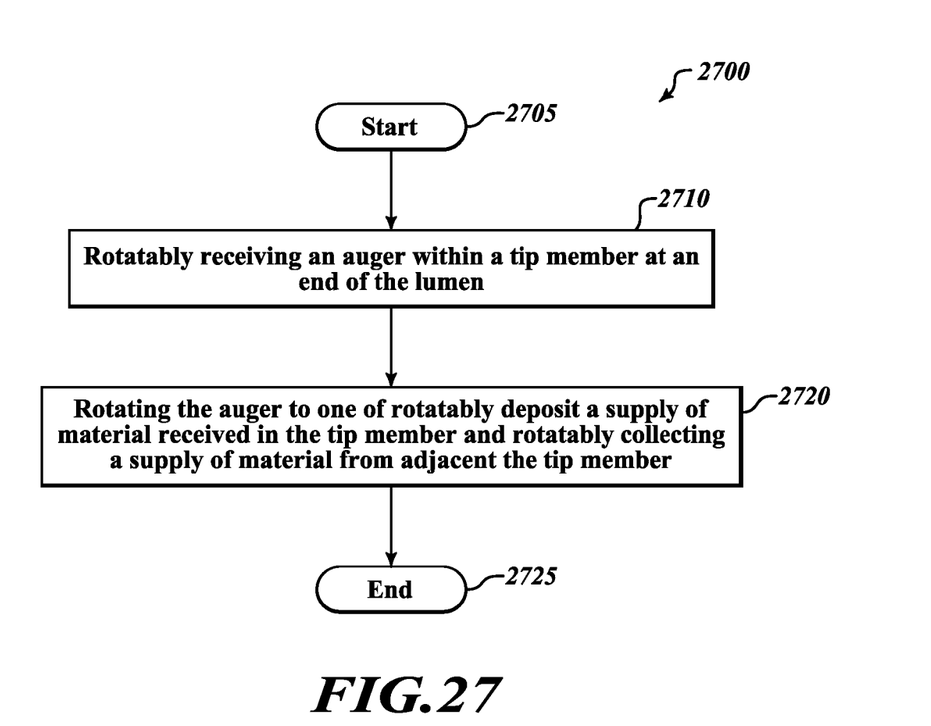
FIG. 27 is a flow diagram of another illustrative method.

Referring to FIG. 27, a flow diagram represents an illustrative method 2700 of using a distal tip that receives a rotatable auger to deposit or collect materials. The method 2700 starts at a block 2705. At a block 2710, an auger is rotatably received within a tip member at an end of a lumen. At a block 2720, the auger is rotated to one of rotatably deposit a supply of material received in the tip member and rotatably collect a supply of material from adjacent the tip member. The method 2700 ends at a block 2725.

It will be appreciated that the detailed description set forth above is merely illustrative in nature and variations that do not depart from the gist and/or spirit of the claimed subject matter are intended to be within the scope of the claims. Such variations are not to be regarded as a departure from the spirit and scope of the claimed subject matter.

What is claimed is:

1. An apparatus comprising:
    a tip body defining a fluid chamber and receiving a stylet through the fluid chamber; and
    a movable member coupleable to the stylet and including a membrane sealably enclosing the fluid chamber, the movable member being configured to move and to open the fluid chamber responsive to extension of the stylet, the membrane configured to release fluid from the fluid chamber upon the extension of the stylet.

2. An apparatus to deliver a fluid to a target tissue location, the apparatus comprising:
    an elongate lumen terminating in a distal tip including a fluid chamber;
    a stylet extending through the elongate lumen into the distal tip and the fluid chamber, the fluid chamber configured to retain fluid between the stylet and an inner surface of the distal tip of the elongate lumen, the stylet distally extendable to open the fluid chamber; and
    a movable member that is affixed to a distal end of the stylet and configured to transition between a sealed state sealing a distal end of the fluid chamber and an unsealed state releasing a fluid from the fluid chamber, the movable member transitionable from the sealed state to the unsealed state through distal extension of the stylet.

3. The apparatus of claim 2, wherein the distal end of the fluid chamber is at least partially covered by the movable member in the form of a membrane.

4. The apparatus of claim 3, wherein the membrane includes a destructible portion configured to be ruptured responsive to being distended by extension of the stylet.

5. The apparatus of claim 3, wherein the membrane includes a semi-permeable member configured to become porous responsive to being distended by extension of the stylet.

6. An apparatus comprising:
    a tip body defining a fluid chamber and receiving a stylet therethrough, wherein the fluid chamber retains fluid surrounding a length of the stylet; and
    a movable member coupleable to the stylet and including a membrane sealably enclosing the fluid chamber, the movable member being configured to move and to open the fluid chamber responsive to extension of the stylet by:
        (i) causing the membrane to prevent release of the fluid from the fluid chamber prior to the extension of the stylet, and
        (ii) (ii) causing the membrane to permit release of the fluid from the fluid chamber upon the extension of the stylet.

7. The apparatus of claim 6, wherein the membrane includes a destructible member configured to be ruptured responsive to extension of the stylet thereby causing the membrane to permit release of the fluid from the fluid chamber.

8. The apparatus of claim 6, wherein the membrane includes a semi-permeable member configured to become porous responsive to extension of the stylet thereby causing the membrane to permit release of the fluid from the fluid chamber.

* * * * *